United States Patent [19]

Kishi

[11] Patent Number: 4,779,612

[45] Date of Patent: Oct. 25, 1988

[54] HYSTEROSCOPE HAVING A FLEXIBLE OPERATION PORTION

[75] Inventor: Yukitoshi Kishi, Omiya, Japan

[73] Assignee: Fuji Photo Optical Co., Ltd., Japan

[21] Appl. No.: 108,468

[22] Filed: Oct. 15, 1987

[30] Foreign Application Priority Data

Nov. 11, 1986 [JP] Japan .................................. 61-268373

[51] Int. Cl.⁴ ................................................ A61B 1/06
[52] U.S. Cl. ................................................. 128/6
[58] Field of Search .................................. 128/4, 6, 20

[56] References Cited

U.S. PATENT DOCUMENTS 3,948,251  4/1976  Hosono ..................................... 128/4
4,562,832  1/1986  Wilder et al. ........................... 128/20
4,630,649  12/1986 Oku .......................................... 128/4 X
4,669,172  6/1987  Petruzzi ................................... 128/6 X

FOREIGN PATENT DOCUMENTS 61-196702 12/1986 Japan .

*Primary Examiner*—William H. Grieb
*Attorney, Agent, or Firm*—Parkhurst, Oliff & Berridge

[57] ABSTRACT

A hysteroscope which allows an operator to perform medical treatments in a through-endoscopic manner. The hysteroscope is free to bend between the operation section and insertion section thereof and is capable of maintaining its bent state as it is, so that the operator can perform observations and operations in a comfortable position.

7 Claims, 3 Drawing Sheets

HYSTEROSCOPE HAVING A FLEXIBLE OPERATION PORTION

BACKGROUND OF THE INVENTION

1. Field of the Invention

The present invention relates to an endoscope suitable for observation of the interiors of a uterus and, in particular, to a so called hysteroscope which allows an operator to operate and observe in a comfortable position.

2. Description of the Related Art

Conventionally, a hysteroscope widely employed in obsterics and gynecology is in the form of a so called rigid scope which is wholly constructed in a rigid manner, that is, in which not only an operation section located at hand is made of a rigid or hard tube but also an insertion section to be inserted into a patient's body is formed of a rigid tube. One of major reasons of the use of the hysteroscope of this kind is that an operational force at hand can be transmitted directly to the leading end of the insertion section with a very high follow-up efficiency. However, as is generally known, when the hysteroscope is used, an operator must operate the hysteroscope at such position as to front on between the stood-up two legs of the patient lying on her back on a medical examination bench. In the conventional rigid hysteroscope, when the operator tries to change his or her position so as to change the leading end of the hysteroscope that is shaped straight, the operator cannot but contact the patient's two legs to limit the movement of the operation section of the hysteroscope so that the interiors of the uterus of the patient cannot be observed all over. Therefore, the advent of a new hysteroscope which can eliminate the above drawback has been desired.

In view of the above-mentioned circumstances, the present patent application proposed and disclosed a new hysteroscope, as a measure to solve the above problem, in Japanese Utility Model Application No. 60-81081 filed on May 31, 1985. For reference, the above-mentioned Japanese Utility Model Application No. 60-81081 was invented by the same inventor of the present patent application and was laid open to public inspection in Japan on Dec. 8, 1986. This publication date is later than the application date of the present patent application in Japan, that is, Nov. 11, 1986, which is the priority date of the present patent application. This new hysteroscope is far advantageous over the conventional rigid hysteroscope in that it is easier to insert and observe.

However, although the new type of hysteroscope has such an advantage as mentioned above, due to the fact that between a rigid tube section forming an insertion section to be inserted into a patient's body and an operation section at hand there is provided, as a part of the insertion section, a flexible portion which can be freely bent, there still exists such a problem as mentioned below. That is, in operating this hysteroscope, an operator must hold the operation section thereof at hand in one hand at the same time, in order to maintain the state of insertion or to advance the insertion of the hysteroscope further, the operator has to hold and operate the rigid tube section, which is a part of the insertion section, in the other hand. Therefore, both hands of the operator are always restrained to hold the hysterscope itself, with the result that it is practically impossible for a single operator to perform other operations, for example, a through-endoscopic (that is, by means of an endoscope) medical treatment, which is a problem to be solved.

SUMMARY OF THE INVENTION

The present invention aims at eliminating the above-mentioned problem found in the prior art hysteroscope.

Accordingly, it is an object of the invention to provide a hysteroscope comprising an operation section at hand and insertion section to be inserted into a patient's body, in which the portion of the operation section adjacent to the insertion section is formed in such a flexible structure as to be capable of maintaining the bent state thereof and a rigid tube section forming the insertion section is connected to the flexible portion of the operation section.

It is another object of the invention to provide a hysteroscope comprising an operation section and an insertion section which are rotatably connected to each other so as to be able to change the direction of the end of the insertion section without altering an operator's attitude in connection with the bent portion of the insertion section.

According to the hysteroscope constructed in the above-mentioned manner, due to the fact that the operation section at hand and the rigid tube portion of the insertion section are connected directly to each other, an excellent follow-up efficiency can be obtained in operation and also the direction of the insertion section can be changed irrespective of the insertion direction of the insertion section, permitting an operator to perform operations in a comfortable portion. In addition, the present invention allows a single operator to observe and perform a through-endoscopic medical treatment or the like at the same time.

BRIEF DESCRIPTION OF THE DRAWINGS

The exact nature of this invention, as well as other objects and advantages thereof, will be readily apparent from consideration of the following specification relating to the accompanying drawings, in which like reference characters designate the same or similar parts throughout the figures thereof and wherein.

DETAILED DESCRIPTION OF THE INVENTION

Detailed description will hereunder be given of the preferred embodiment of a hysteroscope according to the present invention with reference to the accompanying drawings.

Figure 1:
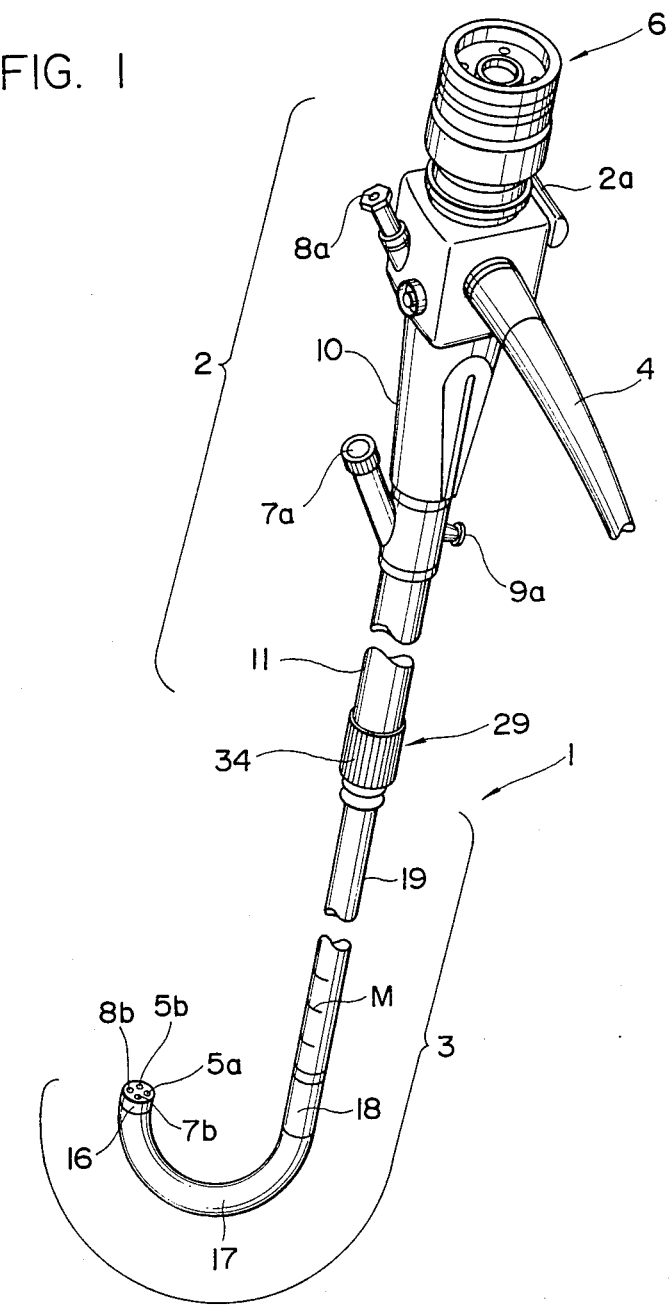
FIG. 1 is an exterior view of an embodiment of a hysteroscope according to the invention.

As shown in FIG. 1, a hysteroscope 1 is composed of an operation section 2, an insertion section 3 and a light guide cable 4. Similarly to a soft type of endoscope which is well known and is referred to as fiber scope, the hysteroscope 1 is provided with an illumination optical system, an observation optical system and a treatment device insertion channel, as well as with a water feed/discharge channel which is used to feed or discharge water. The above-mentioned illumination optical system is used to emit an illumination light from an external light source (not shown), via a light guide optical fiber bundle (not shown) connected removably to the external light source device and extending through the light guide cable 4 and the insertion section 3, from an illumination window 5a provided at the leading end portion of the insertion section so as to illuminate the part to be examined. The above-mentioned observation optical system is composed of an object lens system interposed between an observation window 5b provided in the insertion section 3 leading end portion parallel to the illumination window 5a and an eyepiece section 6 provided in the operation section 2, an image guide optical fiber bundle, and an eyepiece system in a well known manner. Also, the treatment device insertion channel is formed by communicating an insertion port 7a and a projection port 7b respectively provided in the operation section 2 and the leading end portion of the insertion section 3 by means of a flexible tube, and the insertion port 7a is provided with a stopper having a well known valve structure. Further, referring to the water feed/discharge channel that is characteristic of the present hysteroscope and comprises a water feed channel and a water discharge channel, the water feed channel is formed by communicating a water pouring port 8a and a water excurrent port 8b respectively provided in the operation section 2 and at the leading end of the insertion section 3 by means of a flexible tube, and it is used to feed water into a uterus, which is a target to be examined, in a predetermined amount and at a given speed to expand the uterus for easy observation. The water discharge channel serves also as the treatment device insertion channel and includes a water discharge port 9a which is disposed in the operation section 2 and is used to discharge water in such a manner that the amount of water fed into the uterus through the above-mentioned water feed channel can be maintained in a constant level, so that a so-called water feed/discharge can be realized.

Figure 2:
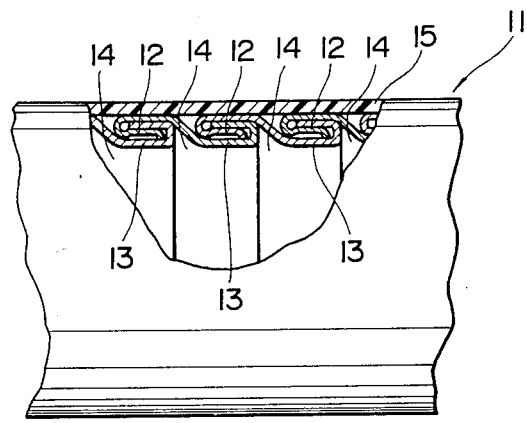
FIG. 2 is a section view of main parts of a flexible portion of an operation section of the above embodiment.

The operation section 2 of the above-mentioned hysteroscope 1 is composed of a grip portion 10 and a flexible portion 11. The flexible portion 11, as shown in FIG. 2, is composed of a large number of short-ring-shaped articulated ring members 14, 14 ---, having the same diameter, and each articulated ring member 14 has an outer periphery the section of which is formed in a flat S shape. The articulated ring 14 is also provided in the two side edge portions thereof with U-shaped, connecting engagement portion 12, 12 which face oppositely to each other. The flexible portion 11 is formed by sequentially securing one connecting engagement portion 12 of an articulated ring member 14 to the other connecting engagement portion 13 of an adjacent articulated ring member 14. Therefore, the flexible portion 11 is free to bend and, at the same time, it is capable of maintaining its state in which it is bent due to a friction produced in the connected and engaged portion thereof when the respective articulated ring members 14, 14, ---are bent with respect to one another. In FIG. 2, reference numeral 15 designates a flexible coating which is made of a synthetic resin material such as urethane or the like.

Figure 3:
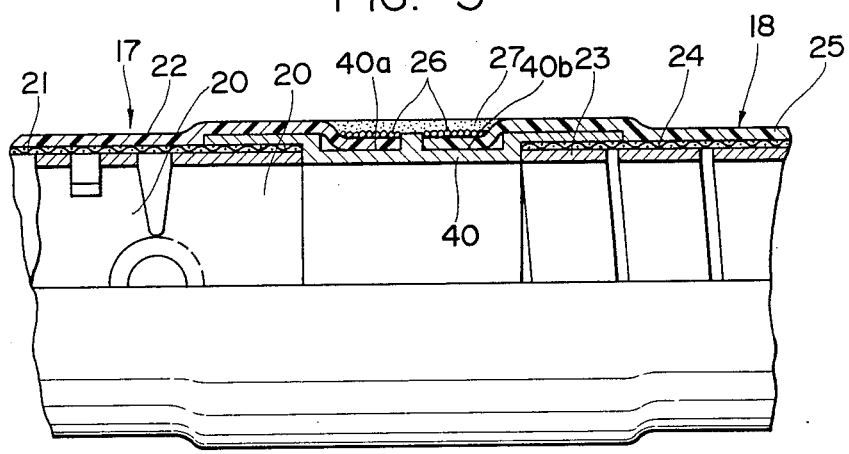
FIG. 3 is a section view of main parts of a connecting portion connecting a bent portion with a soft portion in an insertion portion of the above embodiment.

Referring next to the structure of the insertion section 13, the insertion section 13 is composed of a leading end hard portion 16, a bent portion 17, a soft portion 18 and a rigid tube portion 19 which are connected to one another sequentially in this order, that is, from the leading end thereof. The above-mentioned bent portion 17 can be formed, as shown in FIG. 3, by connecting articulated rings 20, 20, . . . , putting a net 21 made of stainless steel or the like over the outer circumferences of the connected articulated rings 20, and further placing a coating 22 of rubber material or the like over the outer circumference of the net 21. The bent portion 17 can be controllably curved in a vertical direction by rotatively operating an operation lever 2a in the operation section 2 by means of a pair of upper and lower operation wires (not shown) which are well known. Also, in the soft portion 18, there is used, as a core member, a flex which can be made by winding a thin belt-shaped metal plate in a spiral manner. That is, the soft portion 18 can be made by putting a net 24 onto the outer circumference of the abovementioned flex 23 and further placing a coating 25 of urethane or the like over the outer circumference of the net 24. Thus, the soft portion 18 has a flexible structure, that is, it is free to bend. As shown in FIG. 3, the bent portion 17 and the soft portion 18 are connected to each other by means of a tubular connecting member 40. In other words, the above-mentioned articulated ring 20, flex 23, and nets 21, 24 are, as shown, fitted into the respective ends of the connecting member 40 and fixed thereto by soldering, welding, or other similar methods. Also, the respective ends of the coatings 22 and 25 are fitted into circumferential grooves 40a and 40b formed in the outer circumference of the connecting member 40, fixed thereto by a tightening thread 26, and further mold fixed thereto by means of an adhesive.

Next, referring to the above-mentioned rigid tube portion 19, the rigid tube portion 19 is formed of a metal pipe (shown in FIG. 4) which is made of stainless steel and is connected and fixed to the above-mentioned soft portion 18, and the tube portion 19 is coupled to the flexible portion 11 of the above-mentioned operation section 2 by means of couple means to be described later. Further, the rigid tube portion 19 is, as shown in FIG. 1, provided in the outer circumference thereof with a measuring scale M extending in the longitudinal direction thereof and graduated in centimeters, so that the quantity of insertion of the insertion section 3 can be known when it is inserted.

Figure 4:
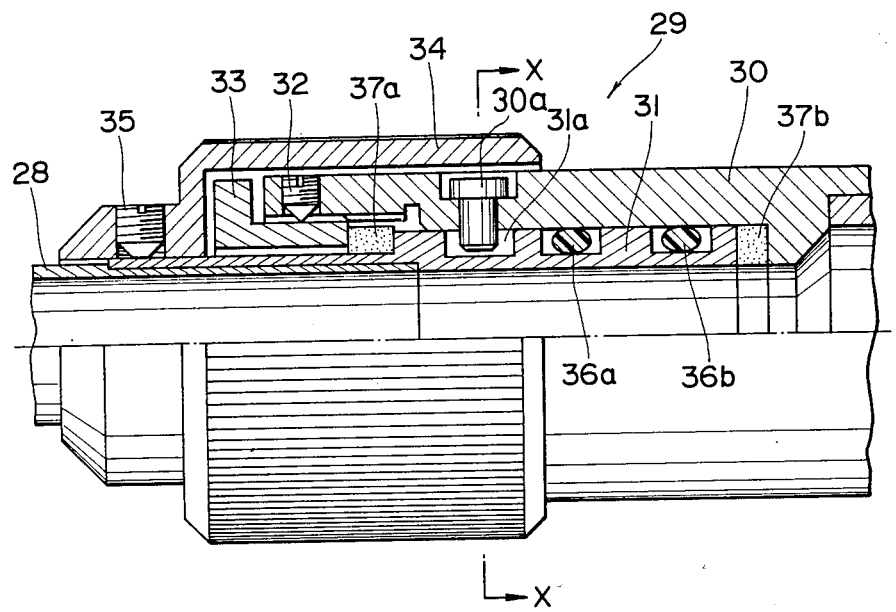
FIG. 4 is a section view of main parts of couple means for coupling a rigid tube portion of the insertion section to the flexible portion of the operation section; and, FIG. 5 is a section view taken along the line X—X in FIG. 4.
Figure 5:
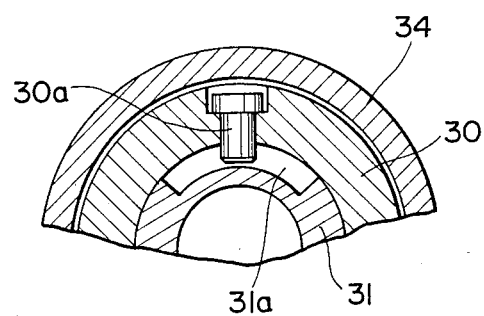

The above-mentioned couple means 29 is constructed in such a manner as shown in FIG. 4. Specifically, in FIG. 4, reference numeral 30 designates a support tube which is fixed to the leading end of the above-mentioned flexible portion 11, and 31 stands for a couple tube which is fixed to the base end of the metal pipe forming the rigid tube portion 19 by means of suitable fixing means such as soldering or the like. The couple tube 31 is fitted into the abovementioned support tube 30 and is prevented from coming off therefrom by a stopper ring 33 which is threadedly connected to the leading end portion of the support tube 30 and fixed thereto by a set screw 32. Also, the couple tube 31 and the support tube 30 are coupled to each other in such a manner that they can be rotated within a restricted range of about 90° with respect to each other, due to the engagement of a circumferential groove 31a formed in the outer circumference of the couple tube 31 in the angular range of about 90° (the angular range is not always limited to about 90°) with a stop pin 30a fixed to the support tube 30, as shown in FIG. 5. In FIG. 4, reference numeral 34 designates a rotary operation knob ring which is fixed to the couple tube 31 by a set screw 35 and is used to integrally rotate the couple tube 31. Further, reference characters 36a and 36b designate O-rings for waterproofing, respectively, and 37a and 37b stand for low friction members of Derlin or the like for reduction of torques produced during rotation, respectively.

The hysteroscope 1 constructed in the above-mentioned manner can be used by connecting water-feed/-discharge-associated pipes and connecting the light guide cable 4 to the external light source device. When inserting the insertion section 3 into a body for observation, due to the fact that by bending the flexible portion 11 at hand in a desired amount the grip portion 10 and eyepiece portion 6 of the operation section 2 can be located at positions displaced out of the axis of the insertion section 3, that is, the rigid tube portion 19, observation and operation can be performed in a comfortable attitude. Also, since the insertion section 3 can be bent individually by operating the operation lever 2a, there is eliminated the need of the operation to twist the whole hysteroscope for all-over observation of the portion to be examined as in the prior art hysteroscopes. Further due to the fact that the flexible portion 11 is structured such that when it is bent the bent state thereof can be maintained as it is, even if an operator lets go one hand off from the rigid tube portion 19, by holding the grip portion 10 of the operation section 2 in the other hand the insertion state of the insertion section 3 can be maintained sufficiently. That is, the operator is able to use treatment devices or the like alone without an assistant.

Obviously from the foregoing description, according to a hysteroscope of the present invention, an operator is able to observe and operate in a comfortable position. Also, the operator is able to operate by himself or herself treatment devices or the like while holding the hysteroscope, permitting the speed-up of observation and treatment.

It should be understood, however, that there is no intention to limit the invention to the specific forms disclosed, but on the contrary, the invention is to cover all modifications, alternate constructions and equivalents falling within the spirit and scope of the invention as expressed in the appended claims.

What is claimed is:

1. A hysteroscope comprising:
    an operation section including a grip and a flexible portion having a following end coupled to the leading end of said grip, said flexible portion being composed of a plurality of articulated ring members, each of said articulated ring members being provided in the circumferential wall thereof with a connecting engagement portion for mutual engagement with its adjoining articulated ring member, said flexible portion being capable of maintaining its bent state as it is;
    an insertion section having a following end coupled to the leading end of said flexible portion of said operation section, at least the portion of said insertion section to the following end of said insertion section being formed in the form of a rigid tube portion;
    an illumination optical system adapted to send the light transmitted from a light cable coupled to said operation section to an illumination portion provided at the leading end of said inserton section so as to illuminate the part of a patient to be examined; and,
    an observation optical system adapted to observe said patient to be examined from an eyepiece portion provided in said operation section through an observation portion provided in the leading end of said insertion section.

2. A hysteroscope as set forth in claim 1, wherein said connecting engagement portion is a portion having an S-shaped section.

3. A hysteroscope as set forth in claim 2, wherein said S-shaped portion of said articulated ring member has two side edges which are respectively formed in a U-like shape and are oriented in the opposite direction with each other.

4. A hysteroscope as set forth in claim 3, wherein said insertion section is provided in the leading end thereof with a bent portion which can be freely bent, and said bent portion can be bent and controlled by means of an operation lever provided in said operation section.

5. A hysteroscope as set forth in claim 4, wherein said insertion section is provided in the leading end thereof with a water excurrent port to which water can be supplied from a water pouring port provided in said operation section, so that water can be supplied from said water excurrent port to the part of a patient to be examined.

6. A hysteroscope as set forth in claim 5, wherein there is formed a projection port in the leading end of said insertion section, there is formed an insertion port in said operation section, and there is formed a treatment device insertion channel between said insertion and projection ports.

7. A hysteroscope as set forth in claim 6, wherein there is formed in said operation section a water discharge port which communicates with said treatment device insertion channel.

* * * * *